United States Patent [19]

Akishika

[11] 4,429,575

[45] Feb. 7, 1984

[54] METHOD FOR INSPECTING A NON-METALLIC OBJECT BY MEANS OF IMPACT ELASTIC WAVES AND ITS APPARATUS

[76] Inventor: Tameyuki Akishika, No. 4384, Totsuka-machi, Totsuka-ku, Yokohama-shi, Kanagawa-ken, Japan

[21] Appl. No.: 298,959

[22] Filed: Sep. 3, 1981

[30] Foreign Application Priority Data

Apr. 24, 1981 [JP] Japan .................. 56-62063

[51] Int. Cl.³ ........................................... G01N 29/04
[52] U.S. Cl. ........................................ 73/598; 73/584
[58] Field of Search ................ 73/598, 579, 584, 12

[56] References Cited

U.S. PATENT DOCUMENTS

| | | | |
|---|---|---|---|
| 3,521,483 | 7/1970 | Miller et al. | 73/598 |
| 3,946,598 | 3/1976 | Towne et al. | 73/12 |
| 4,128,011 | 12/1978 | Savage | 73/579 |
| 4,305,294 | 12/1981 | Vasile et al. | 73/579 |

*Primary Examiner*—Anthony V. Ciarlante
*Attorney, Agent, or Firm*—Louis E. Marn; Elliot M. Olstein

[57] ABSTRACT

This invention relates to a method and apparatus for inspecting a non-metallic object by means of impact elastic waves to measure the thickness of the non-metallic object such as a concrete structure, solid, etc. or to detect foreign matter contained therein. Impact elastic waves are propagated into the non-metallic object by striking an impact plate mounted thereupon with a hammer or the like.

5 Claims, 4 Drawing Figures

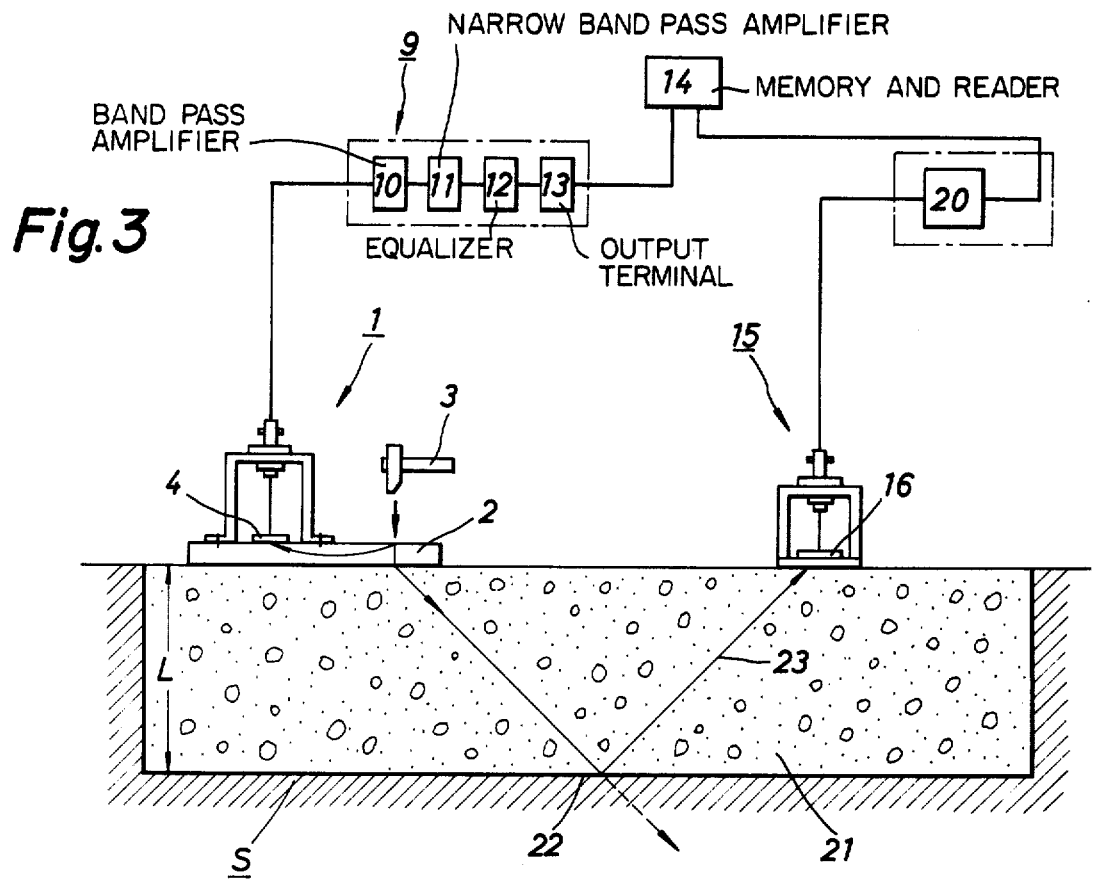
Fig.3
Fig.4
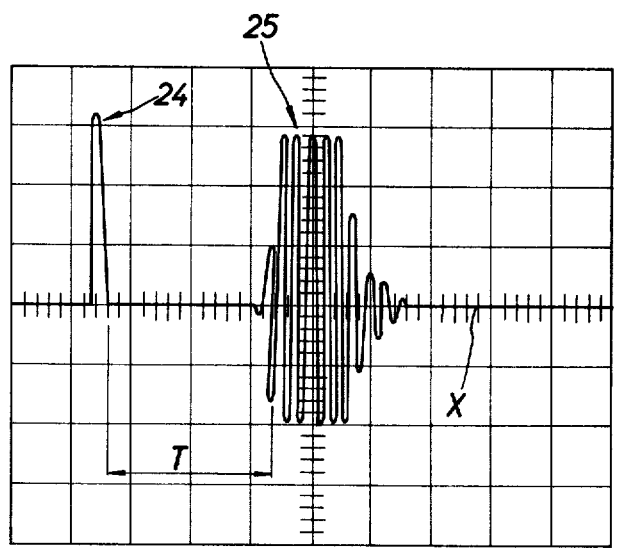

METHOD FOR INSPECTING A NON-METALLIC OBJECT BY MEANS OF IMPACT ELASTIC AND ITS APPARATUS

FIELD OF THE INVENTION

This invention relates to method and apparatus for inspecting a non-metallic object by means of impact elastic waves to measure thickness of the non-metallic object or to detect any foreign matter contained therein.

BACKGROUND OF THE INVENTION

According to a conventional system for inspecting a non-metallic object, impact elastic waves are generated by striking the non-metallic object by a hammer and are received by a microphone or a receiver of a movable coil type, to effect analysis of the non-metallic object.

Such conventional system for inspecting a non-metallic object by means of impact elastic waves experience the following problems since the frequency of impact elastic waves is no more than 1 KHz:

(1) The impact elastic waves pass through small foreign matter contained in the non-metallic object without reflection;

(2) It is difficult to set an accurate generation time for the impact elastic waves; and (3) Inspection is disturbed by other various outside noises.

Further, there is known a system for inspecting a non-metallic object such as a concrete structure by means of ultrasonic pulse of high frequency. In such case, a thick piezoelectric element has been used as a vibrator. Such a technique is disclosed e.g. in Professor J. H. Bungey's article entitled "The Validity of Ultrasonic Pulse Velocity Testing of In-place Concrete for Strength" (NDT International, 1980 December Issue) or Japanese researchers' article entitled "The Estimation of a Thickness of Concrete Structure by Ultrasonic Pulse Method" (Japanese technical periodical "Suiyokai-shi" 1980 May Issue).

The ultrasonic pulse method is greatly dependent upon the range of frequency. A normal frequency to be used for this method is limited to the range of from several ten KHz to several hundred KHz and requires a considerably thick piezoelectric element.

When inspecting soil or a concrete structure in which material density is irregular and components are rough, the ultrasonic pulse method has the following deficiencies:

(1) An efficient reflection of the ultrasonic pulse is not attainable because the object is non-metallic; and (2) Efficiency for converting electric signals into mechanical vibration is extremely low.

SUMMARY OF THE PRESENT INVENTION

Accordingly, the present invention relates to a method and apparatus for nondestructively inspecting a non-metallic object by means of impact elastic waves for the purpose of measuring thickness of the non-metallic object or for detecting any foreign matter contained therein.

First, a mechanical impact is given to the non-metallic object by striking an impact plate mounted thereon by a hammer or the like thereby propagating impact elastic waves into the non-metallic object. The impact plate is provided with a thick piezoelectric element having a frequency exceeding several MHz with the piezoelectric element being connected to an electric circuit. Once the impact elastic waves are propagated, only specific high frequency is selected by the piezoelectric element and converted into pulse signals. The resulting pulse signals are transmitted to a memory and indication means connected to the electric circuit thereby generating time of detection of the impact elastic waves.

On the other hand, a portion of the impact elastic waves propagated into the non-metallic object is reflected from any foreign matter contained therein or from a boundary thereof. A specific high frequency of the reflected elastic waves is separately received by a deflection piezoelectric element having a frequency exceeding several KHz, mounted on another surface of the non-metallic object. The specific high frequency is converted into pulse signals and the pulse signals transmitted to the memory and indication means thereby generating a time of detection of the reflected waves which can be compared with receiving time of the impact elastic waves in the memory and indication means.

Other and further objects, features and advantages of the invention will appear more fully from the following description.

BRIEF DESCRIPTION OF THE DRAWINGS

FIG. 3 is a general view of a use condition of the invention mounted on a surface of a concrete structure buried in a soil; and FIG. 4 is a graph of the wave forms which were indicated by an oscilloscope in order to measure the thickness of the concrete structure.

DETAILED DESCRIPTION OF THE INVENTION

Figure 1:
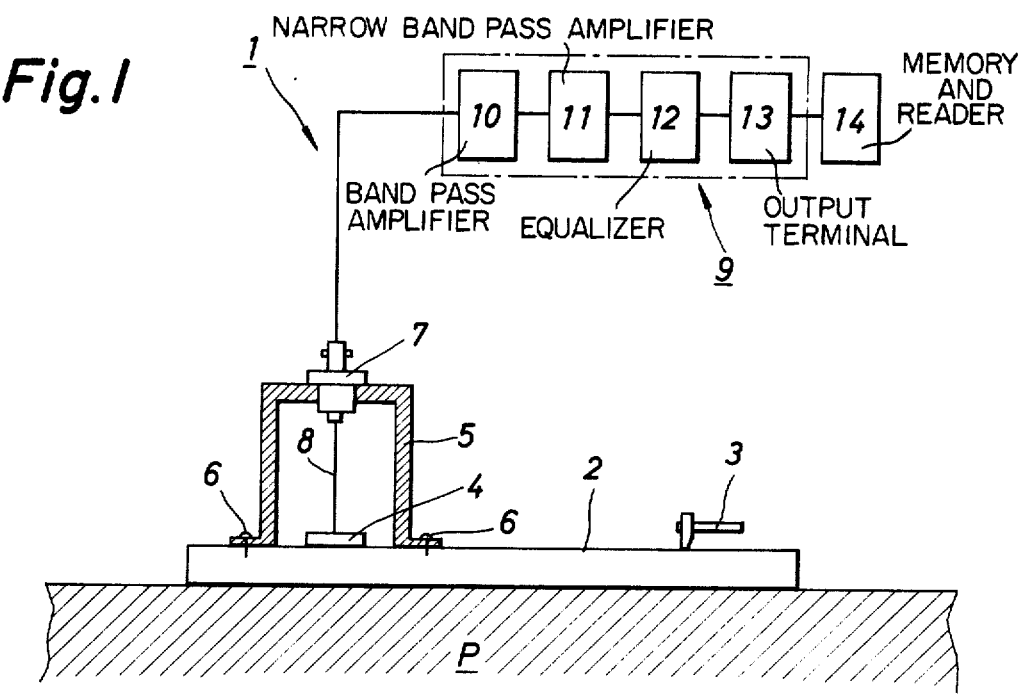
FIG. 1 is a front view of and a block diagram of an impact elastic wave generating time receiver in an apparatus according to the present invention.

Referring now to FIG. 1, there is shown an impact elastic wave generating time receiver 1 including an impact plate 2 made of, e.g. steel. The impact plate 2 is mounted on a non-metallic object P, such as a concrete foundation, soil or like non-metallic structure. A hammer 3 is provided for striking the impact plate 2 and may be replaced by a small steel ball or a steel bar. To the impact plate 2, there is affixed a thick piezoelectric element 4, such as by means of an adhesive or screws. The piezoelectric element 4 is disposed within a case 5 and mounted to a surface of the impact plate 2 by screws 6. A connector 7 is positioned within a hole in the upper surface of the case 5 with an electric wire 8 connected to a terminal (not illustrated) of the piezoelectric element 4 and to an electric circuit 9.

The electric circuit 9 is used for converting a frequency responding to the piezoelectric element 4 into steeply rising pulse signals and is comprised, in series, of a frequency tuning circuit 10 for extracting only a frequency exceeding several MHz, a single frequency tuning circuit 11 consisting of a specific frequency obtained by selecting further the high frequency extracted by the frequency tuning circuit 10 in order to prevent malfunction due to noises, a waveform correcting circuit 12 for converting the specific frequency into acute pulse signals and an output terminal 13 for generating the output of the pulse signals.

A memory and indication means 14 is connected to the output terminal 13 and may be comprised of, e.g. an oscilloscope or a time counter or the like.

Figure 2:
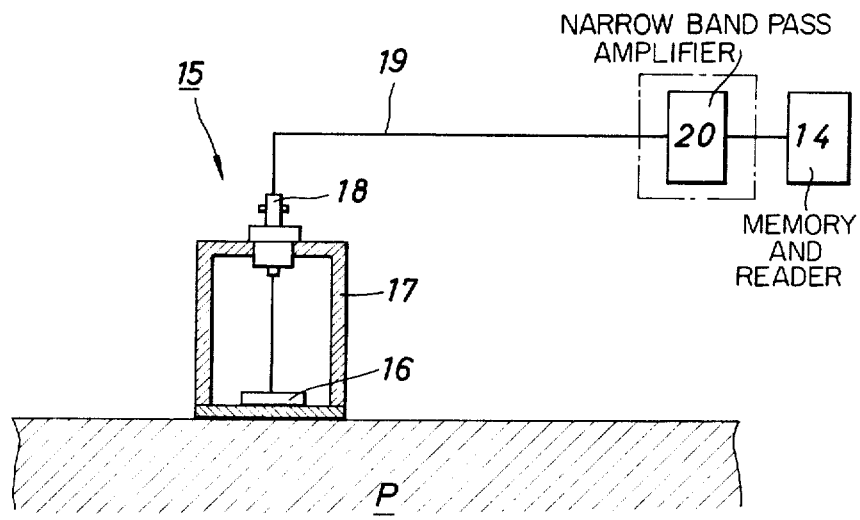
FIG. 2 is a front view of and a block diagram of a reflection wave receiver.

Referring to FIG. 2, there is shown a reflection wave receiver 15 for receiving reflected waves out of the elastic waves propagated into the non-metallic object P by striking the impact plate 2. A deflection piezoelectric element 16 responding to a frequency exceeding several KHz is disposed in a case 17 and is fixed to the bottom of the case 17 by means of adhesives or the like. A connector 18 is installed through a hole in the top of the case 17. An electric wire 19 is provided for connecting the deflection piezoelectric element 16 to a single frequency selecting and amplifying circuit 20 by way of connector 18.

The single frequency selecting and amplifying circuit 20 is an electric circuit for selecting and amplifying a specific single frequency out of the electric signals of the reflected waves transmitted from the deflection piezoelectric element 16. The reflection wave receiver 15 is constructed so that reflected waves thus selected may be entered into the memory and indication means 14.

Operation of the present invention will now be described with reference to measuring the thickness of a concrete structure 21 buried in a soil S. The impact elastic wave generating time receiver 1 is placed on an exposed surface of the concrete structure 21 and the impact plate 2 struck by the hammer 3. Due to mechanical impact, impact elastic waves having a wide range of frequencies are propagated into the impact plate 2. Out of the impact elastic waves, only a high frequency exceeding several MHz is converted into electric signals by the piezoelectric element 4 of the impact elastic wave generating time receiver 1 with the electric signals being transmitted by way of the wire 8 to the frequency tuning circuit 10, and further to the single frequency tuning circuit 11. Accordingly, a specific single frequency is selected from which the noise causing erroneous motions is completely removed. Subsequently, the specific single frequency is converted into steeply rising pulse signals by means of the wave form correcting circuit 12 and the latter transmitted from the output terminal 13 to the memory and indication means 14.

Referring to FIG. 3, impact electric waves are propagated from the impact plate 2 into a concrete structure 21, but certain high frequencies exceeding several MHz out of the impact electric waves are rapidly attenuated and relatively lower frequencies advanced to deeper portion of the concrete structure 21. When a part of the relatively lower frequencies reaches a boundary 22 between the concrete structure 21 and soil S, a portion thereof is propagated into the soil itself, but another portion thereof is reflected. Reflected waves 23 are received by the deflection piezoelectric element 16 of the reflection wave receiver 15.

The frequency of the deflection piezoelectric element is several KHz. Unlike the thick piezoelectric element 4, the deflection piezoelectric element is vibrated in a wave form in a horizontal direction and may selectively respond to the frequencies ranging from several KHz to several ten KHz, whereby it is possible to selectively catch the waves of the frequency band most suitable for any non-metallic object having a coarse structure. The vibration of the reflected waves thus obtained are converted into pulse signals and the latter transmitted to the single frequency selecting and amplifying circuit 20.

The pulse signals thus selected and amplified are transmitted to the memory means 14 where it is possible to effect a display on a fluorescent screen of a Braun tube, as shown in FIG. 4. Therefore, if a time T from a pulse signal 24 at the impact wave generating time to a pulse signal 25 of the reflected wave is read on a time axis X, the thickness L of the concrete structure 21 can be determined by making use of propagation velocity of the impact elastic wave which has been measured in advance.

While a reflection method of the impact elastic waves have been described, the present invention is not to be limited to such a reflection method. For instance, by mounting a transmitter and a receiver on both sides of the non-metallic object to be inspected, the inspection method according to the present invention may be carried out.

Further, although the impact plate 2 is mounted horizontally upon the non-metallic object in FIGS. 1 and 3, the impact plate 2 may be mounted vertically, in which case, the impact plate 2 is secured to the non-metallic object.

In summary, the present invention produces the following effects:

(1) By striking an impact plate mounted on a non-metallic object with a hammer or the like, impact elastic waves having large energy can easily be propagated into the depth of the non-metallic object;

(2) Since a frequency exceeding several MHz out of the impact elastic waves are caught immediately by a thick piezoelectric element affixed to the impact plate, it is possible to accurately set a generation time of the impact elastic waves, so that measurement is not affected by any outside noises; and (3) Since a reflection method of the impact elastic waves is introduced, the present invention can contribute greatly to detect existence of any foreign matter contained in the non-metallic object or to measure the thickness thereof. The range of the frequency most suitable for the reflection method is 1 KHz to 50 KHz, a range not used for in this technical field.

What is claimed is:

1. Method for inspecting a non-metallic object by means of impact elastic waves comprising:

propagating impact elastic waves into the non-metallic object by giving a mechanical impact to an impact plate mounted on the non-metallic object;

receiving selectively a frequency exceeding several MHz out of the impact elastic waves immediately by a thickness piezoelectric element;

detecting and memorizing electrically a generating time of the impact elastic waves by converting into pulse signals a specified higher frequency extracted from the selectively received frequency exceeding several MHz;

receiving selectively by a deflection piezoelectric element a frequency exceeding several KHz out of the elastic waves propagated into the non-metalic object and reflected from an opposite boundary thereof or from any foreign mater contained therefrom;

detecting and memorizing electrically the propagated and reflected impact elastic waves by converting into pulse signals a specified higher frequency extracted from the selectively received frequency; and the memorized generating time of the impact elastic waves being compared with a receiving time of the reflected impact waves, thereby a thickness of the non-metallic object being measured or any foreign matter contained therein being detected.

2. Apparatus for inspecting a non-metallic object by means of impact elastic waves comprising:

an impact plate mounted on a surface of the non-metallic object;

a thickness piezoelectric element having a proper frequency exceeding several MHz, which is connected to the impact plate;

a first electric circuit for converting into pulse signals the impact elastic waves responding to the thickness piezoelectric element as a result of striking the impact plate;

memory and indication means for memorizing and indicating a generating time of the impact elastic waves by means of the pulse signals;

a deflection piezoelectric element responding to a frequency exceeding several KHz in the impact elastic waves propagated into the non-metallic object and reflected from an opposite boundary thereof or from any foreign matter contained therein; the deflection piezoeletric element being mounted on an other surface of the non-metallic object, and a second electric circuit for converting into pulse signals the reflected waves responding to the deflection piezoelectric element;

the second electric circuit being connected to the memory and indication means in which a generating time of the impact elastic waves is able to be compared with a receiving time of the reflected waves.

3. Apparatus as claimed in claim 2, wherein the first electric circuit comprises a frequency tuning circuit, a single frequency tuning circuit, a wave-form correcting circuit and an output terminal, all of which are connected to each other in series.

4. Apparatus as claimed in claims 2 or 3, wherein the thickness piezoelectric element is connected to the frequency tuning circuit by way of a wire and the memory and indication means is connected to the output terminal by way of a wire.

5. Apparatus as claimed in claim 2, wherein the second electric circuit is a single frequency selecting amplifying circuit which is connected to the memory and indication means by way of a wire.

* * * * *